United States Patent [19]

Gerard

[11] 4,311,137
[45] Jan. 19, 1982

[54] INFUSION DEVICE

[75] Inventor: William L. Gerard, Milwaukee, Wis.

[73] Assignee: Sherwood Medical Industries Inc., St. Louis, Mo.

[21] Appl. No.: 126,806

[22] Filed: Apr. 30, 1980

[51] Int. Cl.³ .................. A61M 5/00; A61M 25/00
[52] U.S. Cl. .................... 128/214.4; 128/DIG. 16
[58] Field of Search ................. 128/214.4, 221, 347, 128/214 R, 214 F, DIG. 16

[56] References Cited

U.S. PATENT DOCUMENTS

| | | | |
|---|---|---|---|
| 3,707,972 | 1/1973 | Villari et al. | 128/274 X |
| 3,739,778 | 6/1973 | Monestere, Jr. et al. | 128/214.4 |
| 3,757,771 | 9/1973 | Ruegg et al. | 128/214.4 X |
| 3,766,916 | 10/1973 | Moorehead et al. | 128/DIG. 16 X |
| 3,851,647 | 12/1974 | Monestere, Jr. et al. | 128/214.4 |
| 3,853,127 | 12/1974 | Spademan | 128/214.4 |
| 3,880,401 | 4/1975 | Wiltse | 128/214 R X |
| 4,073,297 | 2/1978 | Kopp | 128/214.4 |
| 4,231,367 | 11/1980 | Rash | 128/214.4 |

*Primary Examiner*—Gene Mancene

*Assistant Examiner*—Robert P. Swiatek
*Attorney, Agent, or Firm*—Stanley N. Garber; William R. O'Meara

[57] ABSTRACT

A fluid administration device is provided which includes a catheter holder having a passage extending through it, a plastic cannula connected at the distal end of the passage, an elastomeric seal at the proximal end of the passage, and a fluid administration side port intermediate the ends of the passage. The device includes a needle holder having a needle cannula extending through the seal, passage, and into the catheter. When the needle holder is in its initial position, the seal is in a passage venting position so that a source of administration fluid can be connected to the side port and the device flushed of air. When the air is removed, the needle assembly is moved to an armed position forcing the seal into a compressed condition in the passage. After the catheter has been placed into the vein, the needle is withdrawn proximally from the catheter holder with the plug sealing the proximal end of the passage.

25 Claims, 4 Drawing Figures

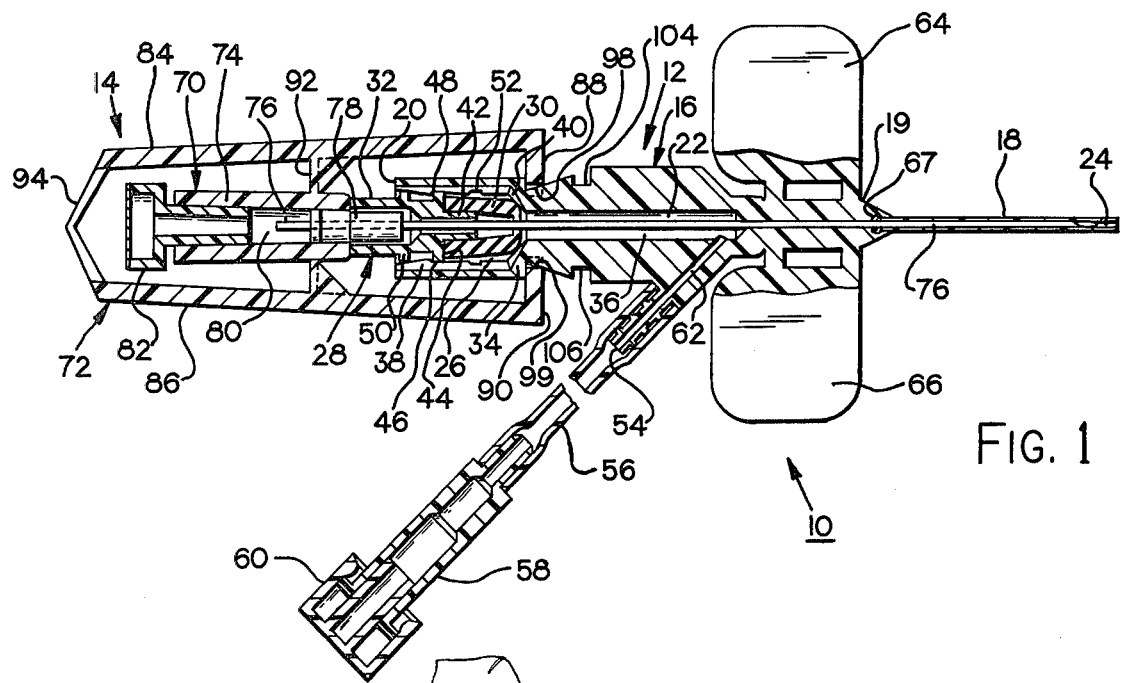
FIG. 1
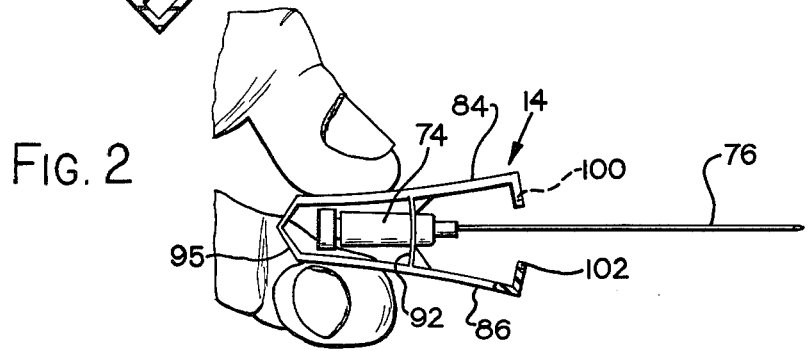
FIG. 2
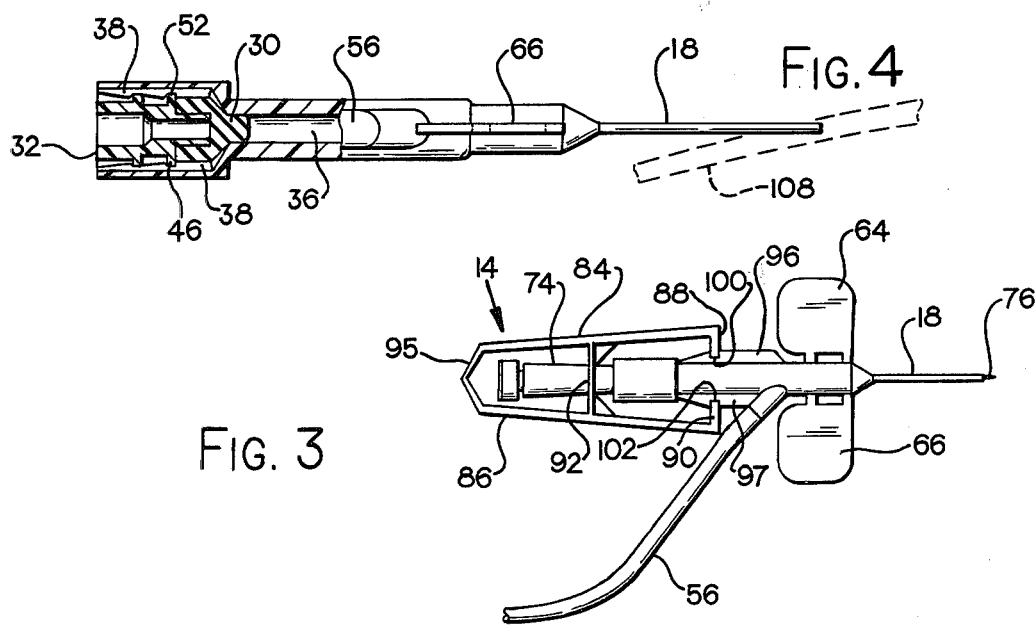
FIG. 4
FIG. 3

4,311,137

INFUSION DEVICE

BACKGROUND OF THE INVENTION

This invention relates to fluid administration or infusion devices and more particularly to such devices which include catheter placement units.

Intravenous fluid administration devices often include a holder carrying a plastic catheter and a removable needle cannula extending through the catheter and past the distal tip of the catheter for inserting the needle and catheter through the skin and into a body vessel, such as a vein of a patient. If the venipuncture is successfully performed, the needle is removed and a source of infusion liquid, such as glucose, blood, saline solution, or other liquid, is connected to the holder to supply the infusion liquid to the vein.

Air must, of course, be removed from the catheter placement device, and the infusion liquid source connected to it without introducing air into the device in order to avoid any air being introduced into the vein of the patient. Generally, after the venipuncture and removal of the needle, blood is allowed to flush the air from the catheter holder, and a liquid-filled delivery tube from the infusion liquid source is then carefully connected to the blood-filled device.

Performing the above steps without introducing air into the system is relatively tedious, and generally results in blood escaping from the device and soiling clothing or the like or requiring the use of absorbant materials to catch the escaping blood. Also, the above connection of the infusion liquid source to the device requires manipulation of parts while the catheter is in the vein of the patient, and this tends to increase patient discomfort and the danger of damage to the patient.

SUMMARY OF THE INVENTION

Accordingly, it is an object of the present invention to provide an improved fluid administration device wherein the above disadvantages are substantially obviated and to provide an improved method of connecting a source of infusion fluid to the vascular system of a patient.

In accordance with one form of the present invention, there is provided a catheter holder having a passage therethrough, a catheter at the distal end of the holder connected with the passage, an elastomeric seal adjacent the proximal end portion of the holder, a fluid inlet port connecting with the passage between the seal and the catheter, and a needle assembly having a needle cannula extending into the catheter. The seal is movable between a passage venting position and a passage closing position.

In accordance with another aspect of the invention, a method of connecting a source of infusion liquid into a vessel of a patient is provided. The method includes providing a catheter holder having a catheter, a side infusion port in the holder, a movable seal in the holder, and a needle extending into the catheter. The side port is connected to a source of infusion liquid and the device is purged of air while the seal is in a venting position in the holder. Then the seal is moved to a passage sealing position and the needle and catheter are inserted into the patient. The needle is removed from the holder while maintaining the catheter in the patient and the holder connected to the source of infusion liquid.

These, as well as other objects and advantages of the invention, will be apparent from the following detailed description and accompanying drawing.

BRIEF DESCRIPTION OF THE DRAWING

FIG. 1 is a top view in cross-section of an intravenous fluid administration device in accordance with a preferred embodiment of the present invention;

FIG. 2 is an illustration, on a reduced scale, showing the needle holder of FIG. 1 as it is withdrawn from the catheter holder;

FIG. 3 is a top plan view on a reduced scale of the device of FIG. 1 but with the device in the armed condition; and FIG. 4 is a side view, partly in cross-section, of the catheter holder of FIG. 1 after it has been inserted into the vein of a patient and the needle holder has been removed.

DESCRIPTION OF THE PREFERRED EMBODIMENT

Referring now to the drawing, and particularly to FIG. 1, an intravenous fluid administration device or catheter placement unit 10 is shown including a catheter holder 12 and a needle holder 14.

The holder 12 has a main body 16, and a plastic catheter 18 connected to the distal end 19 of body 16 which extends distally from the holder. The holder 12 has an open proximal end 20 and a passage 22 extending through the body from the proximal end 20 to the lumen 24 of catheter 18. Passage 22 has an enlarged bore portion 26 adjacent the proximal end 20 of the body 16 which receives a movable seal assembly 28 that includes an elastomeric closure seal or plug 30 and a relatively rigid piston 32. The seal 30 is pierceable by a needle and is of a relatively soft rubber or plastic material which is compressible and generally of the type that is self-sealing at the point of penetration when a needle is withdrawn from the seal. The seal 30 is shown cup-shaped with its closed end distally of its open end. Piston 32 is disposed on the proximal side of the seal 30 and is slidable in bore 26. The seal 30 is disposed between piston 32 and a conical distal end wall 34 of the bore 26, which wall connects with a main passage portion 36 of passage 22.

The seal assembly 28 is shown in FIG. 1 in its initial position in which the passage 22 is vented to atmosphere at the proximal end 20. The inner walls of bore 26 are provided with circumferentially spaced ribs or spacers 38, and the conical end wall 34 with circumferentially spaced ribs or spacers 40. Spacers 38 and 40 provide fluid flow passageways between the seal assembly 28 and the inner walls of bore 26 and conical wall 34 so that the passage 22 is vented to atmosphere through the open end 20 of the holder.

The piston 32 has a distal end 42 of reduced diameter which extends into the cup-shaped seal 30, and an annular distal end wall 44 which engages the proximal open end wall of seal 30. The peripheral portion 46 of wall 44 serves as a peripheral abutment or detent which is disposed, in FIG. 1, in detent slots 48, one in each of the longitudinal ribs 38. The piston also has a proximally spaced, annular wall 50 forming a detent. Sections of the ribs 38 are distally inclined radially inwardly from the end 20. The annular walls 44 and 50 frictionally hold the piston 32 in place until it is manually moved. Another plurality of detent grooves 52 spaced distally from detent slots 48 are provided to receive the peripheral detent wall 46 when the piston is moved distally relative to body 16 from its initial position shown in FIG. 1 to a second or armed position described hereafter.

The body 16 is also provided with a side infusion port 54 adapted to receive an infusion liquid through a rubber or plastic tube 56 having its distal end frictionally connected to port 54. Tube 56 has a luer connector 58 connected to its proximal end for receiving a complementary luer connector of an infusion set or infusion liquid source (not shown). A removable closure cap 60 is shown closing the end of connector 58. The infusion port 54 is connected by a passageway 62 in body 16 to the body passage 22, passageway 62 intersecting or connecting with the passage 22 at a location axially between the catheter 18 and seal 30.

The catheter holder body 16 is also provided with a pair of diametrically opposed flat wings 64 and 66 which, in use, may be adhesively taped to the skin of the patient at the venipuncture site to maintain the device stationary during infusion.

The catheter 18 is provided with an enlargement 67 which fits within a corresponding recess in the body 16 to insure that the catheter will not become detached during use. The body 16 may be insert molded about the catheter end enlargement 67.

The needle holder 14 includes a needle assembly indicated generally at 70 and a latching handle member 72 for manually holding the needle assembly and positioning and latching it in a desired position relative to catheter holder 12. In FIG. 2, the needle holder 14 is shown manually held and detached from the catheter holder 12, as will be further discussed herein.

The needle assembly 70 of FIG. 1 is shown including a needle hub 74, preferably transparent, and a needle 76 shown as a needle cannula. Needle 76 has a ferrule 78 connected to it such as by a conventional crimping operation. The ferrule 78 is secured to hub 74 such as by a suitable cement or by other suitable means. The hub 74 is hollow and has a chamber 80 in fluid communication with the lumen of needle 76. A hollow closure cap 82 is shown closing the proximal end of chamber 80. The cap 82 may be slidable into and at least partially out of the hub chamber 80. When partially out of chamber 80, it vents the chamber to atmosphere so that during venipuncture, blood can readily flow into the hub 74 and provide a visual indication of a successful venipuncture. Alternately, if desired, the cap may be provided with an air-permeable membrane at the proximal end of the cap which is impermeable to blood.

The handle 72 of the needle holder includes a pair of generally longitudinally extending elongate arms 84 and 86 having integral depending detents 88 and 90 respectively at the distal ends of the arms. The arms 84 and 86 are integrally connected to the needle hub 74 by an integral connection 92 intermediate their ends. A pair of integral flexible end struts 94 (FIG. 1) and 95 (FIG. 2) connect the proximal ends of the arms together.

As best seen in FIG. 3, the body 16 has a pair of opposed, flat elongate walls 96 and 97 extending outwardly from the body. The detents 88 and 90 are normally resiliently urged by arms 84 and 86 against the edges of walls 96 and 97 of the body in depressions 98 and 99 of the walls 96 and 97 which hold the catheter and needle holders 12 and 14 axially in an initial position or relationship in which the distal tip of needle 76 is proximal of the distal tip of catheter 18. The bottom edges of detents 88 and 90 are provided with grooves 100 and 102 that straddle the edges of walls 96 and 97 to maintain the needle holder 14 against rotation relative to the catheter holder 12.

When the proximal ends of arms 84 and 86 are pressed toward each other, such as indicated in FIG. 2, the arms tend to pivot on connector 92 and the opposite or distal ends spread apart. When the pressure on the proximal ends is removed, the distal ends move toward each other due to the resilience of the parts of the needle holder 14.

The catheter holder body walls 96 and 97 are also provided with detent grooves 104 and 106 spaced distally of depressions 98 and 99. These grooves are adapted to receive the detents 88 and 90 when the needle holder 14 is moved to the armed position, the position shown in FIG. 3, and which is discussed hereafter. The side walls of detent grooves 104 and 106 maintain the needle holder 14 in the armed condition until manually released.

The catheter holder body 16 and the needle holder 14, except the stainless steel needle 76 and metal, such as aluminum ferrule 78, are preferably made of a suitable plastic such as polypropylene or the like. These plastic parts are preferably molded of relatively rigid plastic material but flexible where required. The catheter 18 may be made of a suitable plastic such as Teflon, nylon, polyethylene, or the like, and may be made x-ray opaque where desired by employing barium sulfate as a filler in the plastic material used, for example, to mold or extrude the catheter. When the device 10 is removed from its package (not shown), it is in its initially unarmed condition shown in FIG. 1. The cap 60 is removed and the luer connector 58 is coupled in fluid tight connection to a luer coupling element of an intravenous infusion (IV) solution source which, when above the device 10, will supply solution to the inlet port 54. The solution and air will flow through tube 56, passageway 62, into passage 22, then distally along passage 22 and into any spaces between the needle 76 and the catheter 18, and then out the distal end of catheter 18. The infusion liquid and air will also flow in passage 22 proximally along passage portion 36 and between the seal assembly 28 and the ribs 38 and 40 in the enlarged passage portion or bore 26, and then out the proximal end 20 to the atmosphere.

After all of the air is removed from the holder 12, and while the passage 22 is filled with infusion liquid, the needle assembly 14 is grasped by the latching arms 84 and 86 and moved distally relative to the catheter holder 12 until the detents 88 and 90 snap into the grooves 104 and 106 in the holder body 16. The needle holder 14 is then in the armed position with the distal end of needle 76 extending slightly distally of the distal end of catheter 18, the condition shown in FIG. 3. During movement of the needle assembly from the unarmed to the armed condition, the distal end portion of the needle hub 74 moves the piston 32 which, in turn, moves the deformable seal 30 distally in the passage 22 forcing a distal portion of the seal from the enlarged bore 26 into passage portion 36 to sealingly close off the distal end portion of the catheter holder about the needle 76. When the needle holder is moved to the armed position, the piston detent 46 snaps into the detent grooves 52 in the side walls of bore 26 (FIG. 4) to latch the seal 30 in place. The cap 82 may be loosened or moved proximally from its shown position in the hub chamber 80 to vent the hub 74 prior to performing a venipuncture so that blood can readily flow into the hub.

With the armed device 10 purged of air and connected to an infusion liquid source, the distal end of the needle 76 and catheter 18 are inserted through the skin and into a vein or other vessel of the patient. Blood flow into the transparent needle hub is indication of a successful venipuncture. Because the detents 88 and 90 are in the detent grooves 104 and 106, the needle assembly 14 will not move proximally of the catheter holder 12 during venipuncture. After the venipuncture is performed, the needle hub cap 82, where required, may be moved back to a position in which it closes the hub 74.

With the catheter properly disposed in the vessel or vein, the needle holder 14 is preferably removed from the catheter holder 12 while holding the wings 64 and 66 flatwise against the skin of the patient with one hand. The proximal end portions of the detent arms 84 and 86 are squeezed toward each other between the index finger and thumb of the other hand (FIG. 2) to move the detents 88 and 90 outwardly from the grooves 104 and 106 in the body 16. Under these conditions, the needle holder 14 is moved proximally straight out of the catheter holder and discarded. The catheter holder 12 will then be disposed in the vein, such as indicated at 108 in FIG. 4. The infusion liquid is then supplied through the infusion port 54 and through catheter 18 to the vein of the patient at the desired flow rate.

In device 10, when the needle holder 14 is moved to its armed condition (FIG. 3), a portion of the seal 30 is simultaneously forced and compressed into passage 22 about the needle 76. When the needle 76 is removed from the seal 30, the compressive forces acting on the seal readily force the walls of the hole caused by the needle to close. Thus, even though the needle 76 extends through the seal 30 prior to use and during storage and would otherwise tend to cause the hole to remain open, the hole caused by the needle upon removal of the needle is completely closed to thereby sealingly close the proximal end of the catheter holder from the atmosphere.

The seal 30 may be formed of a suitable latex, silicone, rubber, soft plastic or other elastomeric material or combination of materials. Preferably, seal 30 is made of a suitable conventional elastomer or plastic material which is normally self-sealing when a needle is inserted and then removed from the seal.

The cap 60 may be used to temporarily close tube 56, for example, where it is desired to transport the patient while maintaining the catheter 18 in place.

The connection of a source or bottle of infusion liquid with a vein of a patient is greatly simplified by use of the device 10. Because the administration set or source of infusion liquid can be connected to the device 10 and the device purged or air prior to making the venipuncture, there is less manipulation of parts after venipuncture and less chance of damaging the patient. Since the couplings between the device 10 and liquid source can be accomplished before venipuncture, these couplings can be made without fear of damage to the patient. Also, the removal of the needle assembly 70 is facilitated, since it can be simply moved straight out of the catheter holder.

As various changes can be made in the above construction of the method without departing from the scope of the invention, it is intended that all matter contained in the above description and shown in the accompanying drawing shall be interpreted as illustrative and not in a limiting sense.

What is claimed is:

1. A fluid administration device for introducing infusion liquid to a blood vessel of a patient comprising a catheter holder including a body having a passage extending therethrough, a catheter connected to said body in fluid communication with said passage and having a distal portion extending from the distal end of said body, movable seal means in the proximal end portion of said passage, a port connected with said passage at a point between said distal portion of said catheter and said seal means for introducing infusion liquid to said passage and catheter, and a needle extending in said passage and movable to an armed position in which said needle extends in said catheter and distally of the distal end of said catheter for inserting the distal ends of said needle and catheter into a patient, said needle being movable from said armed position and out of said catheter and body, said seal means normally being in a first position in said passage in which liquid can flow from said port and passage past said seal means to the atmosphere while said needle is in said passage to permit the purging of air from said body to a second position in which said passage is sealed from atmosphere at the proximal end portion thereof after said needle is removed from said body.

2. A fluid administration device comprising a catheter holder including a body having a passage extending therethrough, a plastic catheter connected to the distal end portion of the body in fluid communication with said passage, movable seal means in the proximal end portion of said passage, said body having a port connected with said passage at a location between the distal end of said catheter and said seal means for introducing infusion liquid into said passage and catheter, said seal means being movable from a first position in which said passage is vented to atmosphere at the proximal end portion thereof to permit purging of air from said body to a second position in which said seal means sealably closes the proximal end portion of said passage, and a needle assembly carried by said body and movable between first and second positions relative to said body and removable from said body, said needle assembly including engagement means thereon engageable with said seal means, and a needle extending through said seal means and into said passage and catheter, said seal means being movable between said first and second positions thereof in response to movement of said needle assembly between said first and second positions thereof.

3. The device of claim 2 wherein said needle is sized such that when said needle assembly is in said first position thereof the distal tip of said needle is proximal of the distal tip of said catheter and said distal tip of said needle is distally of said distal tip of said catheter when said needle assembly is in said second position thereof.

4. The device of claim 2 wherein said needle is a cannula, said needle assembly includes a needle hub connected in fluid communication with said needle for receiving blood from said needle when said needle is inserted into a blood vessel of a patient, said hub being transparent at least in part to provide a visual indication of said blood.

5. The device of claim 4 wherein said engagement means is said hub.

6. The device of claim 4 wherein said hub is vented to atmosphere to permit blood flow into said hub through said needle.

7. The device of claim 4 wherein said body and said hub are formed of plastic.

8. The device of claim 2 wherein said seal means includes an elastomeric plug and a relatively hard piston engaged and moved by said engagement means when said needle assembly is moved from said first position to said second position thereof to urge said plug in closing sealing engagement in said passage, said plug being self-sealing upon removal of said needle assembly from said body to maintain said passage sealably closed at the proximal end portion thereof.

9. The device of claim 8 wherein the walls of a proximal portion of said passage include first latching means, and said piston includes second latching means thereon movable into latching engagement with said first latching means to fix said plug in said closing sealing engagement in said passage when said needle assembly is moved from said first position to said second position thereof.

10. The device of claim 2 wherein said needle assembly includes longitudinally extending and radially inwardly urged resilient detent means connected intermediate the opposite ends thereof to said hub, said body having latch means for receiving said detent means when said needle assembly is moved to said second position thereof, said detent means being manually releasable from said latch means to permit removal of said needle assembly from said body.

11. The device of claim 10 wherein said detent means includes a pair of elongate arms, a pair of detents on the distal ends of said arms, respectively, which are normally resiliently biased toward each other and movable into said latch means, said detents being movable outwardly away from said latch means in response to manually applied inward forces on the proximal ends of said arms to permit removal of said needle assembly from said body.

12. The device of claim 11 including flexible connection means connecting the proximal end portion of said arms together.

13. The device of claim 2 wherein said port includes luer connection means for connection with complementary luer connection means to connect a fluid administration set to the device.

14. The device of claim 2 wherein said body includes a pair of opposed wings adapted to be adhesively connected with a patient after the catheter has been inserted into the patient.

15. The device of claim 2 wherein the proximal end portion of said passage is enlarged and contains said seal means when in said first position thereof, the walls of said enlarged portion having spacer means spacing said seal means from portions of said walls to maintain said passage vented to atmosphere, detent means on said seal means, detent means on said walls engageable with said detent means on said seal means when said needle assembly is in said second position thereof.

16. The device of claim 2 wherein said seal means comprises a deformable elastomeric seal.

17. The device of claim 2 wherein said needle assembly includes abutment means, and said holder includes abutment means, said needle assembly and holder abutment means being in engagement when said needle assembly is in said second position thereof to prevent proximal movement of said needle assembly relative to said holder during insertion of said needle and catheter into a vessel of a patient.

18. The method of connecting a source of intravenous liquid with a blood vessel of a patient comprising the steps of providing a catheter holder having a passage therethrough open to the atmosphere at the proximal end, an elastomeric seal in the proximal end portion of the passage and movable from a passage venting position to a passage closing position, a catheter connected to said holder and having a distal end portion extending therefrom, and a needle assembly having a needle extending through a portion of said seal and into said catheter, and an administration fluid inlet port connecting with said passage at a location between said catheter end portion and said seal, connecting a source of liquid to said port, with said seal in the venting position and with said needle extending therethrough causing liquid to fill said passage and flush substantially all air from said passage, moving said seal into the passage closing position to compress said seal portion and close said passage while said passage is filled with the liquid, then inserting the distal ends of said needle and catheter into a blood vessel of a patient while said passage is filled with the liquid, while maintaining said catheter in the vessel, withdrawing said needle assembly from said holder, and supplying liquid to said catheter and vessel through said inlet port to the blood vessel.

19. The method of claim 18 wherein said needle assembly is movable distally to an armed position relative to the catheter holder so as to move the distal end of the needle distally of the distal end of the catheter, and effecting said step of moving the seal by moving the needle assembly to the armed position.

20. A fluid administration device comprising a catheter holder including a body having a passage extending therethrough, a catheter connected to said body in fluid communication with said passage and having a distal portion extending from the distal end of said body, a movable seal in the proximal end portion of said passage, a port connected with said passage at a point between said seal and said distal portion of said catheter for introducing infusion liquid to said passage and catheter and a needle movable to a position in which said needle extends in said catheter and distally of the distal end of said catheter for inserting the distal ends of said needle and catheter into a patient, said needle being movable from said position and out of said catheter and body member, said seal being movable from a first position in which fluid can flow from said port and passage past said seal to the atmosphere to permit the purging of air from said body to a second position in which said passage is sealed from atmosphere at the proximal end portion thereof, said passage including an enlarged chamber at the proximal end portion thereof connecting with a smaller passage portion of said passage distally thereof, said seal being disposed in said chamber when in said first position thereof and including an elastomeric plug having at least a portion thereof forceable into said smaller passage portion in response to a force applied thereto for moving said seal from said first position to said second position, said seal including a piston member slidable in said chamber to move said plug to thereby move said seal from said first position to said second position thereof, said chamber having latching means on the walls thereof, said piston member having latching means thereon movable relative to said chamber into a latched position with said latching means on said chamber walls to latch said seal in said second position thereof.

21. The method of connecting a source of intravenous fluid with a blood vessel of a patient comprising the steps of providing a catheter holder having a passage therethrough open to the atmosphere at the proximal end, an elastomeric seal in the proximal end portion of the passage and movable from a passage venting position to a passage closing position, a catheter connected to the holder and having a distal end portion extending therefrom, and a needle assembly having a needle extending into said catheter, and an administration fluid inlet port connecting with said passage at a location between said catheter end portion and said seal, connecting a source of liquid to said port, with the seal in the venting position causing liquid to fill said passage and flush substantially all air from said passage, moving said seal into said passage closing position while said passage is filled with the liquid, then inserting the distal ends of said needle and catheter into a blood vessel of a patient while said passage is filled with the liquid, while maintaining said catheter in the vessel, withdrawing said needle assembly from said holder, and supplying a liquid to said catheter and vessel through said inlet port to the blood vessel, said needle assembly being movable distally to an armed position relative to said catheter holder so as to move the distal end of said needle distally of the distal end of said catheter, and effecting said step of moving said seal by moving said needle assembly to the armed position.

22. The method of claim 21 including providing a piston engaged with the seal having detent means thereon latchable with detent means on the walls of the passage, and moving the piston distally relative to the holder to move the piston detent means into latching engagement with the passage detent means prior to insertion of the needle and catheter into the vessel of a patient.

23. The method of claim 21 wherein the proximal and distal ends of said passage are coaxial, said needle extends through an opening in the seal, and said step of moving the seal includes deforming the seal by forcing a portion thereof from a relatively large part to a relatively small part of said passage to close said small part of said passage and effect compressive forces on said seal portion so that when the needle assembly is removed from the holder said compressive forces insure closure of said opening through the seal.

24. A fluid administration device for introducing infusion liquid to a blood vessel of a patient comprising a catheter holder including a body having a passage extending therethrough, a catheter connected to said body in fluid communication with said passage and having a distal portion extending from the distal end of said body, a deformable elastomeric seal means in the proximal end portion of said passage, a port connected with said passage at a point between said distal portion of said catheter and said seal means for introducing infusion liquid to said passage and catheter, a needle movable to an armed position in which said needle extends in said passage and said catheter and distally of the distal end of said catheter for inserting the distal ends of said needle and catheter into a blood vessel of a patient, said needle normally passing through a hole in a portion of said seal means and being movable from said armed position and out of said catheter and body, said seal means normally being in a first position in said passage in which fluid can flow from said port and passage past said seal means to the atmosphere while said needle is passing through said hole to permit the purging of air from said body, means for deforming said seal means while said needle is passing through said hole into a second position in which said passage is sealed from atmosphere at the proximal end portion thereof and said seal means portion is compressed to ensure closure of said hole when said needle is removed therefrom, and means for securing said seal means in said second position.

25. The device of claim 1 or 24 wherein said seal means is deformed into said second position thereof in response to movement of said needle to its armed position.

* * * * *